United States Patent [19]

Calcaterra et al.

[11] Patent Number: 4,810,567

[45] Date of Patent: Mar. 7, 1989

[54] ANTIMICROBIAL FABRICS UTILIZING GRAFT COPOLYMERS

[75] Inventors: Lidia T. Calcaterra, Des Plaines; Louis J. DeFilippi, Mt. Prospect, both of Ill.; Michael E. Childs, Medford, N.J.; Edwin J. Latos, Chicago, Ill.

[73] Assignee: UOP, Des Plaines, Ill.

[21] Appl. No.: 94,767

[22] Filed: Sep. 10, 1987

Related U.S. Application Data

[63] Continuation-in-part of Ser. No. 768,090, Aug. 21, 1985, abandoned.

[51] Int. Cl.$^4$ .............................................. D03D 3/00
[52] U.S. Cl. .................................. 428/224; 8/115.52; 8/116.1; 8/196; 424/78; 428/264; 428/913
[58] Field of Search ...................... 428/224, 264, 913; 8/115.52, 128 R, 127.6, 196, 116.1; 424/78, 80, 81; 525/426, 445, 455, 502

[56] References Cited

U.S. PATENT DOCUMENTS

| | | | |
|---|---|---|---|
| 3,670,048 | 6/1972 | Magat et al. | 260/857 |
| 4,267,280 | 5/1981 | McCormick | 525/56 |
| 4,343,788 | 8/1982 | Mustacich | 424/78 |
| 4,352,882 | 10/1982 | Maury | 435/101 |
| 4,496,363 | 1/1985 | DeFilippi | 8/115.5 |
| 4,615,937 | 10/1986 | Bouchette | 428/913 |

OTHER PUBLICATIONS

Infection Control, 1(2), 76, Mar. 1980, Textile Res. J., 36, 630 (1966).
Encyclopedia of Polymer Science & Technology, vol. 3, pp. 242–284, Interscience, 1965.
J. App. Polymer Sci., 22, 905 (1978).
Amer. Chem. Soc. Symp. Ser., 187, 33–43 (1982).
Polymer Sci. Technol., 23, 115 (1983), Chem. Abst., 100, 215393z.
Merck Index, 9th E., p. 1297, Biotech. Bioeng., 23, 2885 (1981).
J. Chem. Educ., 58, 168 (1981), Adhesives Age, Dec. 1982, 25–29.

*Primary Examiner*—James J. Bell
*Attorney, Agent, or Firm*—Thomas K. McBride; Eugene I. Snyder

[57] ABSTRACT

A broad class of antimicrobial fabrics result from graft copolymerization of a functionalized vinyl monomer onto a base fabric followed by reaction of the functional group of the graft copolymer, or some derivative thereof, with another functional group of an antimicrobial reagent with formation of a covalent bond. When electron beam irradiation is used to effect graft copolymerization virtually any organic fabric may be used. The multiplicity of functional groups on the graft copolymer also makes possible reaction with several different antimicrobials to afford a broad spectrum antimicrobial fabric.

19 Claims, No Drawings

ANTIMICROBIAL FABRICS UTILIZING GRAFT COPOLYMERS

CROSS REFERENCE TO RELATED APPLICATION

This application is a continuation-in-part of our copending application, Ser. No. 768,090, filed Aug. 21, 1985 now abandoned, all of which is incorporated by reference.

INTRODUCTION

Despite continuing attempts to reduce the overall rate of infection, studies show that one in every fifteen surgical patients still experiences some form of postoperative infection. The risk of infection varies widely with the surgical procedure, with the incidence of infection for some being staggeringly high. New Developments in Infection Control, *Infection Control,* 1(2), 76, March, 1980. An approach to mitigating this problem in a practical manner is represented by the commercial availability of a surgical draping fabric with antimicrobial activity. This material, called ISO-BAC (trademark of American Converters), isolates the surgical incision site and in laboratory tests has achieved a 92-99% kill rate for many common pathogens.

It would be highly desirable to have an antimicrobial fabric bearing one, or some combination of, potent antimicrobial agents. For the purpose of this application an antimicrobial agent is any substance that kills or prevents the growth of a microorganism, and includes antibiotics, antifungal, antiviral, and antialgal agents, but specifically excluding nonspecific antiseptics acting by a general decrease in surface tension, as for example quaternary ammonium compounds. The antimicrobial agent of such a fabric should not be absorbed by the skin or other tissue with which it comes into contact so that relatively toxic agents may be successfully used topically. That is to say, the antimicrobial agent should be strongly bound to the fabric and remain so in use, i.e., have no substantial likelihood of migration from the fabric itself. A second desirable property is that the bound antimicrobial retain a substantial portion of the activity it exhibits in its unbound state. Furthermore, such antimicrobial activity and strong binding to the fabric should be retained over long periods of time so that such a fabric may be readily stored. Finally, any method developed preferably should be suitable for use with a broad variety of common fabrics.

A generalized approach to this problem is discussed in French Pat. No. 2,342,740 which utilizes antimicrobial compounds covalently bound to relatively large molecular entities. This patent discloses the use of many combinations of antimicrobials and solid supports, including some suitable for use as fabrics. Although most combinations employ a direct linkage of the antimicrobial to the solid support, the patent discloses the use of an interposed entity (molecular arm) linking the support to the antimicrobial, and exemplifies several such entities.

The product disclosed in U.S. Pat. No. 4,496,363 utilizes an antimicrobial covalently bound to the fabric so as to maintain the antimicrobial at a distance from the surface, thereby reaping the substantial benefits accruing from keeping the antimicrobial agent away from the fabric surface while still having the antimicrobial firmly bound thereto. The patentee achieved these dual benefits by aminoalkylsilylation of suitable fabrics, covalently bonding one terminus of a polyfunctional spacer moiety to the primary amino functionality, then covalently bonding another terminus to an amino group of an antimicrobial agent.

The invention described herein is another generalized solution to making antimicrobial fabrics. A necessary and essential attribute of our invention is that the antimicrobial remains strongly bound to the fabric at all times, which means the antimicrobial exerts its antimicrobial effect while being covalently bonded to the fabric modified as described within. Our solution is adaptable to a broad class of fabrics, especially cellulosics, and to antimicrobials with diverse functionality. The described invention also is general in the sense that the nature and length of the molecular arm can be readily varied. In particular, the invention here is a method of preparing antimicrobial fabrics by making a graft copolymer of the fabric and a functionalized unsaturated monomer, preferably using electron beam irradiation or redox techniques, and reacting the functional group of the monomer with another functional group on an antimicrobial agent with covalent bond formation. In one variation the functional group of the graft copolymer originally from the monomer is converted to a different functional group prior to reaction with the antimicrobial agent. In another variation the antimicrobial agent is derivatized so as to afford an unsaturated site, with the derivative grafted onto the fabric via the unsaturated center.

BACKGROUND OF THE INVENTION

It has been known for some time that irradiation of cellulose leads to relatively well-defined free radical formation. See, for example, J. C. Arthur, Jr., T. Mares, and O. Hinojosa, *Textile Res. J.*, 36, 630 (1966). But even prior to such structural studies of cellulosic free radicals their chemistry had been utilized to form graft copolymers of cellulose and various monomers using different forms of irradiation (e.g., gamma, X-ray, and ultraviolet) as well as redox systems to generate the cellulose radicals as chain initiators. A comprehensive discussion may be found in an article by E. H. Immergut, "Encyclopedia of Polymer Science and Technology." Volume 3, pp. 242-284, Interscience, 1965.

The particularly careful work of Harris, Arthur, and Carra, *J. App. Polymer Sci.*, 22, 905 (1978) demonstrates some characteristics of particular interest here. Using irradiation absorbed only by cellulose, thereby minimizing homopolymer formation to under about 2%, from 18-72% by weight of glycidyl methacrylate could be grafted onto cellulose. The grafted poly(glycidyl methacrylate) was distributed throughout the cross section of the fibers, but tended to be more concentrated on their outer surface. These workers also found that many other vinyl monomers could be similarly grafted to cellulose.

Graft copolymerization of vinyl monomers onto cellulosic fibers by redox generation of chain initiation is exemplified by the work of Ranby and Gadda, *Amer. Chem. Soc. Symp. Ser.*, 187, 33-43 (1982), who used manganic ions, Mn(III), as the initiator.

In the context of the present application the formation of graft copolymers of cellulose is important as a means of functionalizing cellulose, i.e., modifying cellulose so that the resulting product becomes chemically reactive, especially toward biologically active materials. Other means of functionalizing cellulose have long been known, as for example, conversion of cellulose to carboxymethylcellulose where carboxyl groups are introduced as functional groups, and conversion of cellulose to contain amino-substituted aromatic groups, with subsequent formation of a diazotized cellulose derivative. For convenience as well as conceptual distinction the two kinds of functionalized cellulosics will be referred to as graft copolymers (where the functional group is introduced by graft copolymerization) and as derivatives (where the function group is introduced by a monomeric reagent chemically bonded to cellulose).

Functionalized cellulosics have been investigated in the immobilization of biologically active materials such as enzymes and antimicrobials. Simionescu and Dumitriu (*Polymer Sci. Technol.*, 23, 115 (1983)) explored several cellulose derivatives for immobilization of enzymes via covalent bonding of the functional group of the derivatized cellulose with the enzyme. Antibiotics also were immobilized by covalent bonding to cellulose modified with diazotized amino aromatic groups by reaction of the antibiotic with the diazonium group. However, poly(acrylic acid) grafted cellulose was used to immobilize antibiotics only via ionic bonds, i.e., salt formation accompanying ion exchange. In somewhat related work 6-aminopenicillinic acid (idem., ibid.) and ampicillin (Simionescu and coworkers, *Chem. Abst.*, 100, 215393z), were covalently bound via their amino groups to Biozan R, a xanthan gum having free carboxyl groups (*Merck Index*, 9th Ed., Merck and Co., Rahway, N.J., p. 1297; U.S. Pat. No. 4,352,882), in the presence of water-soluble carbodiimides as condensing agents.

Other functionalized fabrics also have been used to immobilize biologically active materials. For example, polyacrylate has been irradiation grafted onto hydrolyzed nylon and subsequently hydrolyzed to afford a polyamide-poly(acrylic acid) graft copolymer. Both bovine serum albumin and acid phosphatase were immobilized on the latter using a water-soluble carbodiimide as a condensing agent. C. G. Beddows, J. T. Guthrie, and F. I. Abdel-Hay, *Biotech, Bioeng.*, 23, 2885 (1981).

As previously mentioned, irradiation of cellulose is a general method of generating radicals which initiate polymerization of monomers, thereby leading to graft copolymers. Processes using irradiation are not new to industry and are being utilized increasingly in diverse applications. J. Silverman, *J. Chem. Educ.*, 58, 168 (1981). Particularly cost effective is electron beam technology, which is capable of many variations to best fit the desired application. R. Kardashian and S. V. Nablo, *Adhesives Age*, December, 1982, 25–29. In electron beam technology a flux of electrons whose energy is in the kilo electron volt range impinges on material passing through the electron beam. Collision of the energetic electrons generally causes secondary electron emission from the material, thus creating a multiplicity of free radical centers. One feature of electron beam technology of particular value here is its indiscriminate nature, i.e., the technology can create free radical centers in virtually all organic materials. Another feature of electron beam technology of interest here is that the depth of electron penetration is a function of electron energy, i.e., the lower the energy of the electron beam the less its penetration, and the more free radicals tend to form at or near the surface of the material rather than throughout its bulk. Yet another feature is that the number of free radicals formed in organic material is controlled by the flux of the electron beam, or exposure time of the material to the electron beam of a given flux, or some combination of the two. The latter three features make electron beam technology a powerful tool in creating a variable number of radical centers in virtually all organic materials while controlling the cross sectional distribution of such centers.

In fact, electron beam initiated graft polymerization of N-vinylpyrollidine on a nylon fabric has been described by Magat et al., U.S. Pat. No. 3,670,048, who then complexed iodine to the graft polymer to obtain fabrics with germicidal properties arising from the slow release of iodine, or who reacted the graft polymer with an alkyl halide to obtain a fabric having a multiplicity of quaternary ammonium sites which imparted an antiseptic effect arising from its being a surface active agent (i.e., detergent). Such antiseptics exhibit non-specific, indiscriminate activity and often are more harmful than helpful in wound healing.

The work of McCormick, U.S. Pat. No. 4,267,280, and Mustacich et al., U.S. Pat. No. 4,343,788, may be briefly mentioned in passing, although neither are considered prior art for the purpose of this invention for both teach a controlled and sustained release of pesticides and carboxylate materials, whereas our invention relies on an antimicrobial remaining firmly bound to the fabric, i.e., our product is characterized by the absence of release or diffusion of an antimicrobial. In McCormick, pesticides are covalently bound to pendant groups of a polymer with the linkages slowly hydrolyzed to release pesticides at a controlled rate. Mustacich teaches the incorporation of carboxylate antimicrobial agents into certain polymers which allow diffusion of such agents from devices fashioned from said polymers to provide a sustained release of antimicrobial agent.

Analogy of our product to an immobilized enzyme also is quite limited. An immobilized enzyme may be active if the substrate can reach the active site by diffusion. However, in our invention it appears necessary that the bound antimicrobial agent not merely contact the microorganism but penetrate its cell wall or outer membrane. The requirements of the underlying immobilizing system affording an expression of antimicrobial activity appear much more stringent and certainly are only poorly understood.

It would appear most desirable for antimicrobial fabrics to have the antimicrobial largely on their surface rather than in their bulk, both for the purpose of maximizing the availability of the antimicrobial as well as minimizing changes in the physical properties of the resulting fabric. It has been known for some time that graft copolymers of cellulose can have the copolymer in the bulk and on the surface of the fiber, and that the relative distribution of the copolymer can be altered and controlled to some extent. By varying the voltage of the electron beam it may be possible to maximize free radical generation at or near the surface leading to maximization of the graft copolymer at or near the surface. By varying the flux of the electron beam it may be possible to vary the extent of graft copolymer formation, thereby leading to optimization of subsequent antimicrobial loading. And since electron beam generation of free radicals is virtually uniformly applicable to organic materials it may be possible to be used in preparing antimicrobial fabrics regardless of the chemical nature of the fabric.

The invention herein is a general method of making antimicrobial fabrics by covalently bonding an antimicrobial to a graft copolymer of a fabric, especially a cellulosic fabric, where the copolymer has a first functional moiety reactive toward a second functional moiety of the antimicrobial. Where the graft copolymer is prepared using electron beam processing there is the advantage that the concentration of the antimicrobial at or near the surface may be varied by altering the copolymer cross sectional distribution via variation in energy of the electron beam. Furthermore, the use of electron beam technology in graft copolymer preparation may be advantageous in controlling the concentration of bound antimicrobial by affecting the amount of copolymer formation via variation of electron flux. Electron beam processing may have additional advantages in its general utility, i.e., virtually any organic fabric should be capable of forming a graft copolymer.

Binding an antimicrobial to a fabric having a copolymer grafted thereto also has certain advantages irrespective of the method of graft copolymer preparation. Because the antimicrobial is covalently bonded to a functional group of the repeating unit in the copolymer, at least a substantial portion of the antimicrobial will be far from the surface of the fabric and therefore not subjected to undesirable surface effects. Another advantage arises from the copolymer containing many such functional groups in the chain, leading to multiple binding of the antimicrobial to each copolymer chain. This can afford rather high antimicrobial loading where desirable, and offers a means to control antimicrobial loading in any case. Yet another advantage of multiple binding sites on the copolymer chain is the possibility of binding several different antimicrobials along the chain, thereby constructing a "broad spectrum" antimicrobial fabric, i.e., one effective against a broad spectrum of microorganisms.

SUMMARY OF THE INVENTION

The purpose of this invention is to prepare new antimicrobial fabrics. An embodiment is a functionalized graft copolymer of fabric material covalently bonded to one or more antimicrobials. In a more specific embodiment the copolymer results from grafting a vinyl monomer containing at least one reactive functional group onto a fabric material. In a more specific embodiment the graft copolymer results from electron beam irradiation of a fabric impregnated with a vinyl monomer. In another embodiment the fabric is a cellulosic material. In yet another embodiment the grafted copolymer contains a multiplicity of carboxyl groups. In still another embodiment the antimicrobial is bonded to the graft copolymer via formation of an amide linkage. Other embodiments will be apparent from the ensuing description.

DESCRIPTION OF THE INVENTION

Our invention encompasses a very broad, inclusive class of antimicrobial fabrics having one or more antimicrobial agents covalently bonded to a graft copolymer of the fabric. The product can be represented by the structure,

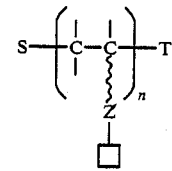

where
S is the fabric,
T is the copolymer end group,
Z is an organic functional group, and
□ is an antimicrobial agent.

What follows is a more detailed description of the products of our invention and various methods of making them. However broad may be the class of the products of our invention, all members share some essential attributes which distinguish and differentiate them from other classes of invention, attributes which make our products particularly noteworthy. We have designed a system where the antimicrobial agent is covalently bound to the modified fabric, and where these covalent bonds are stable (i.e., not hydrolyzed or otherwise broken) under the conditions of product use. We have designed a system where the antimicrobial agent expresses its antimicrobial activity in its bound state, a system characterized by the absence of release or diffusion of the antimicrobial from the fabric. To obtain antimicrobial action from our products by free (unbound) antimicrobial or by release of the antimicrobial agent from the fabric is detrimental to our invention, and in fact steps are taken to ensure the absence of leaching of antimicrobial agent under the intended conditions of its use. It can not be overemphasized that the covalent bond between the first functional group of the graft copolymer and the second functional group of the antimicrobial remains intact throughout the intended use of the fabric.

The underlying fabrics or fibers are subject to enormous variation. It may be that virtually any organic fabric can be used when the final product is prepared via X-ray, gamma, or electron beam irradiation. One desirable class of fabrics consists of cellulosics, as exemplified by cotton, linen, rayon, and cellulose acetate, and in many respects the cellulosic fibers, and especially cotton, are preferred in the practice of this invention. Other fabrics which may be used include silk, wool, and synthesis such as polyamides, polyesters, acrylics and modacrylics, polyolefins such as polypropylene, polyvinyl chloride, poly(vinylidene chloride), poly(vinyl alcohol), poly(hydroxyacetic acid ester), polyurethanes, polytetrafluoroethylene, and copolymers of the above, phenolic type fibers (phenol-formaldehyde condensates), and polybenzimidazole fibers. See, e.g., Kirk-Othmer, "Encyclopedia of Chemical Technology," Third Edition, V. 10, J. Wiley & Sons, Inc., 1980, pp. 148, 181.

There is then made a graft copolymer of the underlying fabric or fiber thereof and a vinyl monomer having a first functional group. The sole requirements of the vinyl monomer are that it form a graft copolymer with the underlying fabric and that the functional group introduced thereby either reacts, or can be chemically converted to another functional group which reacts, with a second functional group on an antibiotic so as to form a covalent bond. The vinyl monomers of this invention have the general structural unit, C=C X, where X is a functional group such as a carboxyl, amino, epoxy, a halogen, isocyanate, carbonyl, nitrile, or hydroxyl moiety. Among these the carboxyl, amino, and epoxy moieties are somewhat preferred.

Examples of functionalized vinyl monomers which may be used in the practice of this invention, and which are given solely for illustrative purposes and are not intended to be exhaustive, include acrylic acid, methacrylic acid, the alkyl esters of these acids, especially their glycidyl esters, acrylonitrile, acrylamide, N-vinylphthalimide allylamine, 4-amino-1-butene, p-aminostyrene, as examples of unsaturated amines, 5-carbonylamino-1-pentene, as illustrative of an unsaturated isocyanate, 3-pentene-2-one, illustrating an unsaturated carbonyl compound, 2-chloroethylvinyl ether, p-chloromethylstyrene, 1-chloro-5-hexeneone-2, to exemplify unsaturated reactive halides, p-hydroxystyrene and 2-butene-1,4-diol as illustrative of an unsaturated hydroxyl-containing vinyl monomer. Polyfunctional vinyl monomers, such as maleic acid and anhydride, also may be used.

Formation of the graft copolymer may be by any method known in the art, but generally will be performed either by irradiation or by a redox system. Irradiation includes gamma, X-ray, ultraviolet, and electron beam irradiation. Electron beam irradiation is greatly preferred as a method because it is the most cost effective, it has general applicability, and is readily adaptable to commercial production of the products of this invention. The dosage and electron beam energy will vary with the fabric as well as the fabric-monomer combination. Both the dosage and energy need to be sufficiently high to effect graft copolymerization, yet not so high as to degrade either the fabric or the monomer, or cause excessive polymerization in the copolymer or excessive homopolymerization. The energy of the electron beam generally will be in the range from about 150,000 to about 3,000,000 electron volts, with a dose generally being in the range from about 0.5 to about 20 megarads (Mrad). It needs to be emphasized that the appropriate energy and dosage will be determined only with routine experimentation, and that both variables can be used to alter somewhat the resulting product. So, for example the depth of the graft may be controlled by the energy of the beam while the amount of copolymer and the extent of its polymerization is affected by the dosage.

Where graft polymerization is initiated by a redox system any suitable oxidizing agent will suffice. Suitable redox systems often operate via 1-electron transfers, and examples of reagents which may be used, although not necessarily with equivalent results, include hydrogen peroxide, the ferrous ion-hydrogen peroxide couple, the hydrogen peroxide-thiourea couple, cerium(IV) salts, especially ceric ammonium salts as ceric ammonium nitrate and ceric ammonium sulfate, the diethyaluminum chloride-Co(III) couple, azoisobutyric acid dinitrile, Cr(VI) salts, and potassium persulfate. Grafting generally is effected by soaking the fabric with a suitable redox agent, then contacting the material with the monomer to be graft polymerized.

The graft copolymerization may be done either on the fabric or the fibers thereof. That is, the finished fabric in the form of, for example, a piece of gauze or a bolt of cloth, may be graft copolymerized with a suitable vinyl monomer. Alternately, the fibers or individual filaments or strands of the fabric, may be graft polymerized and the fabric made thereafter.

Generally the fabric, or fiber thereof, and vinyl monomer are coirradiated. That is to say, the fabric or fiber is soaked in a solution of vinyl monomer. Generally the solvent will be chosen as to cause swelling of the fabric, which is to say the solvent and, presumably, the monomer in solution penetrates into the bulk of the fabric. Suitable solvents include water, alcohol, dimethylformamide, dimethyacetamide, esters, ketones, paraffins, and aromatics. Solvents containing vinylic groups or other polymerizable functionalities are to be avoided. The fabric soaked with vinyl monomer is then irradiated as described previously.

A variant employs preirradiation of the fabric followed by its contact with the vinyl monomer, most usually in solution. In principal this method is advantageous because the radicals originate solely from the fabric, and addition of the radical to the vinyl monomer followed by chain propagation should lead to graft copolymerization virtually to the exclusion of homopolymerization. However, in practice the radicals originating from the fabric often have insufficient lifetime for this technique to be practical.

As briefly stated above, using the technique of electron beam irradiation as an example, the energetic electrons cause secondary electron emission from the fabric, thereby generating discrete radical centers on the fabric. Such radicals add to the vinylic monomer, with subsequent chain propagation of the new radical via its addition to other molecules of vinyl monomer. The radical chain is eventually terminated, and the result is a copolymer of the vinylic compound grafted onto the fabric.

Chain termination may occur by any one of a variety of usual chain terminating processes. For example, chain termination may occur by the radical center at the growing end abstracting a labile hydrogen, in which case the end group T will be a hydrogen. Or termination may occur by addition of oxygen to form a peroxy radical which then abstracts a hydrogen, in which case T is the hydroperoxy group, OOH. As another example two radical chains may couple, in which case T represents another vinyl copolymer. Chain termination of polymerization is well understood in the art; the end group T is readily identifiable in the various modes of termination and will not be further discussed here.

Post processing of the graft polymer generally involves washing with a suitable solvent to remove homopolymer which is invariably formed under coirradiation. Generally the homopolymer will be soluble in such solvents as acetone, dimethylformamide, and so forth, whereas the graft copolymer of the fabric remains insoluble.

The process to this point may be summarized by the following equation,

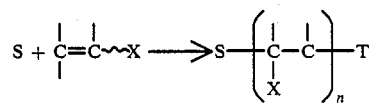

where
S is the fabric or fiber therefrom,
T is the end group of the vinyl copolymer,
X is a functional group which may be carboxyl, amino, epoxy, halogen, isocyanate, carbonyl, nitrile, or hydroxyl, and n is an integer indicating the extent of polymerization of the monomer.

The graft copolymer having a multiplicity of functional groups originating from the monomer is then reacted with an antimicrobial agent so as to covalently bind the latter irreversibly to the graft copolymer while retaining the biological activity of the antimicrobial. The reaction is one between a first functional group of the graft copolymer originating either directly or indirectly from the vinyl monomer and a second functional group of the antimicrobial, the reaction being accompanied by irreversible covalent bond formation. What is meant by the phrase, "originating directly or indirectly from the vinyl monomer," is that the functional group is that of the vinyl monomer or one derived therefrom in a subsequent chemical reaction of the graft copolymer. For example, acrylonitrile may be graft copolymerized on cellulose. The resulting multiplicity of nitrilo groups may be inappropriate for reaction with the desired antimicrobial and may be converted to a multiplicity of carboxyl groups by hydrolysis or aminomethyl groups by hydrogenation. These latter groups may then be more appropriate for further reaction with the antimicrobial.

This reaction of the functional groups on the graft copolymer with those of an antimicrobial may be illustrated by the reaction,

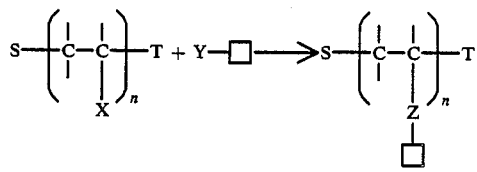

Y is a functional group of the antimicrobial agent and is selected from the same group defining X. Thus, Y may be a carboxyl, amino, epoxy, halogen, isocyanate, carbonyl, nitrile, or hydroxyl moiety. Z represents that functional group which results from covalent reaction of Y and X and which remains intact during the intended use of the antimicrobial fabric. For example, where one member of the X, Y pair is carboxyl and the other is amino the covalent group, Z, formed is the amide group. As another example, where one member of the X, Y pair is epoxy and the other is hydroxyl the covalent group formed, Z, is an ether group. The functional groups represented by Z include all the permutations possible resulting from the covalent reaction of X with Y. Thus, Z includes such groups as amide, ester, urea, urethane, ether, amine, and imine groups.

The symbol □ represents the antimicrobial agents which may be used in the practice of this invention. A working hypothesis is that antimicrobial agents are effective in this invention if they act on the cell wall or membrane either directly or indirectly. This hypothesis is a direct consequence of the desired attribute that the antimicrobial remain strongly bound to the fabric, which requires that the antimicrobial be effective without needing to penetrate beyond the cell wall or membrane of the microorganism.

Within the framework of this hypothesis, examples of antimicrobial agents which may be used in this invention, either alone or in combination, include the polymyxins, bacitracin, circulin, the octapeptins, lysozmye, lysostaphin, cellulytic enzymes generally, vancomycin, ristocetin, the actinoidins and avoparcins, tyrocidin A, gramicidin S, polyoxin D, and tunicamycin. To the extent that the cited hypothesis is inadequate, other antimicrobial agents also might be usable, e.g., the polyene macrolide antibiotics, neomycin, streptomycin, etc. It is not feasible to give here an exhaustive list of potentially useful antimicrobials, but this may be found in compendia such as, "Antibiotics, Chemotherapeutics, and Antibacterial Agents for Disease Control," M. Grayson, Ed., J. Wiley and Sons, N.Y., 1982. Classification of antibiotics by their mode of action may be found in, "The Molecular Basis of Antibiotic Action," Second Edition, E. F. Gale et al., J. Wiley and Sons, N.Y., 1981.

The combination of vinyl monomer used in making the graft copolymer and the antimicrobial agent has important effects on the expressed antimicrobial activity which are not well understood. For example, the graft copolymers of cotton with acrylic acid and with glycidyl methacrylate can be used to immobilize polymyxin with strikingly different antimicrobial activity per gram of immobilized polymyxin. It also has been observed that the equivalent of at least three carbon atoms must separate the fabric from the immobilized polymyxin for the latter to express antimicrobial activity.

After reaction of the antimicrobial with the graft copolymer is complete the product is washed extensively to remove unreacted but adhering antimicrobial agent. Because such antimicrobials often are soluble in water, water often suffices as the wash solvent. But where solubility of the antimicrobial in water is too low to effectively remove the antimicrobial any other suitable solvent may be used. After washing is complete the product is dried and recovered.

The invention herein is subject to many variations, some of which relate to grafting of ethylenically unsaturated antimicrobials directly to the fabric. For example, antimicrobials naturally possessing at least one ethylenic site, such as the polyene macrolide antibiotics, may be coirradiated with the fabric so as to produce a graft copolymer having a multiplicity of antimicrobial nuclei bound thereto. As another example, antimicrobials may be derivatized so as to introduce an ethylenically unsaturated biologically active derivative thereof which may then be graft copolymerized with the fabric. For example, an amino-containing antimicrobial can be reacted with a glycidyl acrylate at the epoxy linkage of the ester portion thereof. The resulting amino hydroxy ester of acrylic acid can then be graft copolymerized onto a suitable fabric. Although in suitable cases such variations may be desirable, or even preferable, they suffer from the disadvantage, at least where graft polymerization is effected by irradiation, that antimicrobial activity of the copolymer often will be reduced through irradiation.

It is to be clearly understood that the examples which follow are but illustrative of the many embodiments of this invention which is not to be limited thereto.

EXAMPLES

Preparation of antimicrobial fabrics will be exemplified largely by a cotton to which is grafted methacrylic acid or glycidyl methacrylate and covalently bonded to polymyxin. The sequence of procedures, each of which is described in greater detail below, is: (1) activation of cotton with methacrylic acid or glycidyl methacrylate (i.e., graft copolymer preparation); (2) immobilization of polymyxin via reaction of amino group of latter with a functional group of the graft copolymer (carboxyl from methacrylic acid, epoxy from glycidyl methacrylate); (3) washing antimicrobial fabric to remove any operationally significant amounts of unbound and releasable polymyxin; (4) determination of amount of polymyxin immobilized on antimicrobial fabric; and (5) determination of antimicrobial effectiveness of fabric.

Removal of Unbound Polymyxin; Leaching Tests

It is essential to remove unbound (i.e., free, or releasable) antimicrobial from the finished product prior to its testing and/or intended use. Stated differently, it is necessary that the effectiveness of the finished product arise solely from the antimicrobial agent covalently bonded to the graft copolymer. This is assured by extensive washing of the antimicrobial fabric follwoed by appropriate testing.

Two tests can be used to establish that no free antimicrobial remains on the fabric which could cause bacterial population reductions: a biological leaching test, and a chemical leaching test. The biological leaching test used to detect diffusion of the antimicrobial is AATCC test method 90-1982, where a sterile swab was dipped into a bacterial suspension and then used to streak an agar plate uniformly over its surface. The microorganisms used were $E.\ coli$ K12K294 for testing of Polymyxin leaching, and $S.\ aureus$ 27217 for testing of lysostaphin leaching. After placing 1" squares of sterile fabrics on AATCC agar seeded with the test bacterium, the plates were placed in a 5° C. refrigerator for 24 hrs. At the end of that period, they were placed in a 37° C. oven for 24 hrs. The degree of leaching was judged by the size in mm of the clear zone around the fabric. Samples were considered free of leaching when not even a hair line of clear zone was observed around the fabric. Only leaching-free samples were tested for antimicrobial efficacy.

The limit of detection must be determined for each combination of antimicrobial and fabric. In the present invention we demonstrated independently that amounts of antimicrobial at or below the detection limit of this test could not lead to bacterial population reductions. This was determined by impregnating the graft copolymerized fabric with amounts of free antimicrobial at and below the detection limit of the leaching test and determining by the FEL test (vide infra) that the fabrics did not show antimicrobial activity.

Another test that was carried out to show that the washed antimicrobial fabrics did not contain effective amounts of free antimicrobial was the chemical leaching test. Here pieces of fabrics with immobilized antimicrobial were exhaustively extracted with a suitable solvent or solution. The extracts were concentrated and analyzed for antimicrobial content. In the case of polypeptide antimicrobials the extracts were hydrolyzed and analyzed for amino acid content. This chemical leaching test confirmed that the detection limit of AATCC 90-1982 was adequate for it to be used as a screening test for the washing procedure of our antimicrobial fabrics.

The chemical leaching test was performed as follows. Two, ten and forty micrograms of polymyxin were absorbed into a 100 cm$^2$ of cotton/polymethacrylic acid activated fabric. The cotton pieces were exhaustively extracted with 1M NaCl solution. The extracts were lyophilized and the residue hydrolyzed to determine the polymyxin content by amino acid analysis. The curve of polymyxin added to cotton/polymethacrylic acid versus polymyxin recovered by extraction was used to establish that samples of immobilized antimicrobial found free of leaching according to AATCC 90-1982 contained less than the minimum concentration of free polymyxin on activated fabric which could give an observable bactericidal effect (FEL 50% or more; vide infra).

The results of the two leaching tests in combination show that the antimicrobial effects of our fabrics must arise from bound, non-diffusable and non-releasable antimicrobial agent.

Bactericidal Effectiveness of Antimicrobial Fabrics

The relative ability of the treated fabric to kill bacteria is called the fabric efficacy level (FEL), which is determined as follows. A 4"×4" square of cloth was folded twice and then a measured volume of bacteria-containing fluid was added to, and adsorbed by, the cloth. The cloth was then incubated in a humid petri dish for a given period of time (usually 30 minutes) after which the cloth was placed in a medium that possessed a pH of 9.0 and shaken vigorously by a mechanical shaker to release the bacteria. A measured quantity of fluid containing the released bacteria was added to an agar medium on a petri dish and the bacterial colonies were counted using a Artek automatic counter.

Minimum Biocidal Concentration of Free Polymyxin on Activated Fabric

For the purposes of this invention the concentration of adsorbed (i.e., free and releasable) polymyxin on activated fabric (cotton/polymethacrylic acid) that yielded 50% bacterial reduction was estimated as follows. Different amounts of polymyxin B sulfate (0, 50, 100, 150, and 200 $\mu$g) in potassium phosphate pH 7 were added to 4"×4" (ca. 1 g) pieces of cotton/polymethacrylic acid. The fabrics were allowed to dry and FEL was determined as described above against E.coli K12K294. The results obtained ranged from 20% to 50% efficacy for polymyxin concentrations ranging from 50-200 $\mu$g per gram of activated cotton, the latter being well within the detection limits of the AATCC 90-1982 leaching test. Therefore samples of immobilized antimicrobial fabrics which after extensive washings are found not to show leaching of antimicrobials under the conditions of the leaching test have less than 50 - 100 $\mu$g of polymyxin per gram of activated fabric, and thus the large antimicrobial activity (90% or more) detected by the FEL test are due to bound antimicrobial.

Cotton, desized and bleached, was used in all the preparations. Methacrylic acid and glycidyl methacrylate were used without purification. Polymyxin B sulfate solutions were made up with sterile water and filter sterilized through a 0.2$\mu$ membrane. Characterization of the activated fabrics was done by IR, and in the case of methacrylic acid the number of carboxyl groups was estimated according to ASTM Designation 1926. The polymyxin content on the finished fabric was calculated from the phenylalanine level as determined from the amino acid content of the products. The stability of the polymyxin solution during binding was followed by high pressure liquid chromatography (HPLC). All the water solutions used were autoclaved, and the rinsing water was deionized water further purified through a Calco system consisting of two deionizer columns, one carbon filter, one bacteria filter, a UV sterilizer and finally a small 0.2$\mu$ membrane filter. The high ionic strength buffer used to remove loosely attached polymyxin was 2M NaCl solution containing 0.1M phosphate buffer at pH 7. The leaching test was performed according to AATCC test method 90-182.

Polymethacrylic Grafted Cotton

In a typical run fifteen 4"×4" pieces of cotton were immersed in 200 mL of 13% methacrylic acid, and left two hours soaking. The pieces were padded dry and individually placed on lead trays, covered with a 1 mL thick polyethlene, and irradiated with an electron beam of 175 KeV at a dose of 5 Mrad on each side. After irradiation they were placed in sterile water and soaked, then successively washed with water at pH 8 three times for one-half hour at a time. IR analysis showed a broad band at 1715 cm$^{-1}$, and sometimes a band also at 1550 cm$^{-1}$.

A molecular weight determination of the grafted polymethacrylic acid was performed as follows. Ten grams of grafted cotton was hydrolyzed in 75 mL of 50% hydrochloric acid at 110° C. in vacuo for 24 hrs. The hydrolyzate was filtered and the filtrate placed in a dialysis tube (MW cutoff ca. 2000) immersed in 2 L of distilled water. The water was changed twice daily during a one-week period, and the dialyzed solution was freeze-dried prior to molecular weight determination. Using size exclusion chromatography with standards for polymethacrylic acid of various molecular weights, the weight-average molecular weight of the grafted polymer was about 2000.

Cotton/Polymethacrylic Acid Grafting by the Preirradiation Method

In this method the cotton pieces were irradiated first with 5 Mrad at 175 KeV on each side and then placed in a solution containing 13% methacrylic acid in water for one hour. Subsequent processing was the same as described above.

Cotton/Polymethacrylic Acid Grafting by a Redox Method

A 0.05 M solution of Ce(NH$_4$)$_2$(NO$_3$)$_6$ in water at pH 1 was deareated and four 4"×4" cotton pieces were soaked in it for five hours. They were then blotted among paper towels and dipped into 15% freshly distilled methacrylic acid in water. The orange color on the cotton disappeared almost immediately indicating the occurrence of a redox reaction. After thoroughly washing the pieces with water, a slight yellowish color remained.

Polyglycidyl Methacrylate Grafted Cotton

Fifteen 4"×4" pieces of cotton were soaked for 2 hours in a 7% solution of glycidyl methacrylate in a methanol(57%)-water(43%) solution. The cotton pieces were irradiated as described above for polymethacrylic acid. The homopolymer formed was extracted with 2-butanone. After extensive drying, the grafted cotton showed an absorption band in the infrared at 1730 cm$^{-1}$ in addition to the normal cotton bands. The epoxide content as determined by the extent of bromination with HBr was 0.16 mmol/g.

Polymyxin Binding to Cotton/Polymethacrylic Acid via 1-Cyclohexyl-3-(2-morpholinoethyl)carbodiimide Metho-p-toluene Sulfonate (CDI)

The immobilization of polymyxin on cotton/polymethacrylic acid was run for 24 hours at pH 6 (potassium phosphate buffer 0.1M) and at room temperature. Glycine ethyl ester was used instead of polymyxin in a control run. All the immobilizations of polymyxin on cotton/polymethacrylic acid reported here were done using 10$^{-2}$ moles/liter CDI and 10 mg/mL polymyxin at a total offering of 1 g polymyxin per g cotton. After the binding, the cotton samples were successively washed with aqueous solutions of (NH$_4$)$_2$SO$_4$ (1M), and phosphate buffer (0.05M), pH 7, in water and sterile water until free of leaching.

The carboxyl content of cotton grafted with methacrylic acid by the different methods described above is summarized in Table 1. Analyses were performed by ASTM D 1926.

TABLE 1
CARBOXYL GROUP CONTENT OF COTTON GRAFTED WITH METHACRYLIC ACID (MA) BY DIFFERENT METHODS

|  | mmoles COOH/g cotton |
|---|---|
| MA Grafted (Mutual Irradiation) | 0.8 |
| MA grafted (preirradiation | — |
| MA grafted (Redox method | 0.4 |

As these data clearly show mutual or coirradiation is vastly superior to redox methods with regard to the amount of monomer grafted. It is also important to note that preirradiation for this fabric-monomer pair results in no detectable grafting, when the operations are performed in air.

The polymyxin content on finished fabrics was calculated from the amino acid content using phenylalanine as the internal standard since there is one phenylalanine per polymyxin. The amino acid determination was done on the solution resulting from hydrolyzing the finished cotton pieces in 50% HCl/H$_2$O under vacuum at 110° C. for 24 hours (the unhydrolyzed cotton was previously filtered off). The amino acid content of a typical run of finished fabric containing polymyxin by mutual irradiation of an MA grafted cotton (see Table I) is shown in Table II, and the polymyxin content of the finished fabrics prepared in this report are listed in Table III. Results of FEL tests from several fabrics are summarized in Table IV.

TABLE II
AMINO ACID ANALYSIS

| Amino Acids | nM/mL | Amino Acids Ratio Expected in Polymyxin | nM/mL Amino Acids Cotton/Poly MA Blank |
|---|---|---|---|
| Aspartic Acids | 9.983 |  | 21.363 |
| Threonine | 945.797 | 2 |  |
| Serine | 40.417 |  |  |
| Alanine | 10.200 |  | 10.885 |
| Valine | 15.922 |  |  |
| Methionine | 21.203 |  | 14.925 |
| Isoleucine | 81.887 |  | 27.526 |
| Leucine | 462.359 | 1 | 24.542 |
| Norleucine | 1003.50 | (internal standard) |  |
| Phenylalanine | 534.654 | 1 | 25.353 |
| Histidine | 11.610 |  | 22.728 |
| Lysine/DABA | 1327.18 | 5 | 109.759 |
| Ammonia | 5030.22 |  | 7370.93 |

TABLE III

POLYMYXIN CONTENT IN FINISHED FABRICS

| Fabrics | mg Polymyxin/g Cotton |
|---|---|
| Cotton/Poly GM | 0.2[1] |
| Cotton/Poly GM/Polymyxin | 1.2 |
| Cotton/Poly MA | 0.2[1] |
| Cotton/Poly MA/Polymyxin | 0.5 |
| Cotton/Poly MA, CDI | 0.7[1] |
| Cotton/Poly MA, CDI/Polymyxin | 22.7 |
| Cotton/Poly MA, CDI/Polymyxin | 25.2 |
| Cotton/Poly MA, CDI/Polymyxin | 40.3 |

[1]This quantity represents the amino acid impurity background derived from the phenylalanine content and expressed in mg of polymyxin.

TABLE IV

FABRIC EFFICACY LEVEL OF FINISHED FABRICS

|  | % Bacteria Reduction | Corrected |
|---|---|---|
| C/Poly MA[1] | 37.8 |  |
| C/Poly MA/Polymyxin |  | 32.1 |
| C/Poly MA, CDI | 51.1 (201)[2] |  |
| C/Poly MA, CDI/Polymyxin |  | 86.4[1] |
|  |  | 96.8[1] |
|  |  | 99.9[1] |
| C/Poly GM | 54 |  |
| C/Poly GM/Polymyxin | 80 |  |

MA = Methacrylic Acid, C = Cotton
GM = Glycidyl Methacrylate
[1]Percent reduction relative to control.
[2]Percent increase.

Table III indicates that the set which was treated with polymyxin and CDI contained upwards of 20 mg polymyxin/g cotton, and Table IV indicates that this set had a large antimicrobial activity. Very much in contrast with these results, the set of fabrics in which the condensing agent (CDI) was omitted, had an amino acid level within the impurity background, which could correspond to no more than 0.7 mg polymyxin/g cotton. This result agreed with the lack of antimicrobial activity (32%) presented by the fabric (Table IV). That the high antimicrobial activity of the immobilized polymyxin on cotton/polymethacrylic acid via CDI was not due simply to an activation of polymyxin by CDI was demonstrated by two results. First, the HPLC trace of polymyxin and CDI in solution is the same as that of polymyxin plus that of CDI indicating that no reaction is taking place between these two reagents in the absence of carboxylic functionalities. Second, the solution of polymyxin plus CDI was lyophilized and its antimicrobial activity shown not to differ from that of polymyxin alone. That a covalent bond between cotton/polymethacrylic acid and polymyxin was formed in the presence of CDI was readily observed by the change in the IR absorbance of the fabric after this treatment, which indicated that the carbonyl absorption due to the carboxylic acid was diminished and amide absorption was increased. Since polymyxin itself has amide bonds, the fact that an amide bond could be formed between a soluble free amino group and the carboxyl group of the cotton/polymethacrylic acid fabric by mediation with CDI was further corroborated by carrying out the immobilization experiment with glycine ethyl ester as a model for a soluble amino group like those of polymyxin. The IR spectrum of the so treated fabric revealed the presence of the amide bond. Since this was not present in either of the reagents used, it can be concluded that it is due to the bond formed between the carboxyl group of cotton/polymethacrylic acid and the amino group of glycine ethyl ester. After washing the samples until no glycine ethyl ester could be observed, the fabric was analyzed for its amino acid content, which at this point could only be derived from bound amino acid. The analysis indicated that indeed glycine was present and therefore had been bound to the fabric by reaction with CDI.

Lysostaphin Binding to Cotton/Polymethacrylic Acid via CDI

Squares (4"×4") of cotton/polymethacrylic acid prepared as described above were soaked in 100 mL of lysostaphin (0.5 mg/mL) in 0.1 M potassium phosphate (pH 6). The dehydrating agent CDI (3 g) was added, and the flask was shaken overnight. The cotton pieces were then washed several times with distilled water, followed by ammonium sulfate (1 M), phosphate buffer, 0.05 M, pH 7, until the fabrics were found free of leaching. Amino acid analysis of the samples indicated binding of about 10 mg lysostaphin per gram cotton.

Fabrics containing bound lysostaphin were tested for antimicrobial properties on V-J agar media. In this test five 1-cm² pieces of fabric were placed on V-J agar to which had been added 10 mL of a 1% solution of potassium tellurite per 60 g agar in 1000 mL water. Staphylococcus species produce acid from mannitol which causes the pH sensitive phenol red to change from red to yellow. Staphylococcus also reduce tellurite to tellurium sulfide, producing black-colored colonies facilitating visualization of growth. The fabric swatches were then challenged with Staphylococcus aureus at five cell concentrations from $7 \times 10^{-4}$ to 1500 colony forming units per cm², and growth was observed at 24 and 48 hours incubation at 37° C. The fabrics described here showed excellent antimicrobial activity at both time periods.

Nylon/Polymethacrylic Acid

Methacrylic acid was graft copolymerized on nylon 6,6 as described above for cotton. The resulting product had a carboxyl content of 0.013 mmole/g. Polymyxin was immobilized onto this grafted nylon as described above to afford a product whose amino acid analysis indicated a content of 0.4 mg polymyxin per gram nylon.

Effect of Reagent Concentration and Antimicrobial Offering

A matrix experiment was performed to determine the effect of CDI concentration and antibiotic concentration on immobilization of polymyxin on cotton/polymethacrylic acid. The activated fabric contained an average of 0.5 mmole carboxyl groups per gram cotton. Nine determinations were made of each FEL test and numbers are those at a 90% confidence level. Six determinations of polymyxin content were performed for each sample with results reported at the 90% confidence level. Results are reported in Table V where $C_p$ is mg polymyxin bound per gram cotton.

TABLE V

REAGENT AND POLYMYXIN CONCENTRATION EFFECTS

| | Polymyxin, mg/mL | | | | | |
|---|---|---|---|---|---|---|
| | 1 | | 5 | | 10 | |
| CDI, g/100 mL | FEL | $C_p$ | FEL | $C_p$ | FEL | $C_p$ |
| 0.3 | 74 | 10.9 | 91 | 12.6 | 88 | 10.3 |

TABLE V-continued

REAGENT AND POLYMYXIN CONCENTRATION EFFECTS

| CDI, g/100 mL | Polymyxin, mg/mL | | | | | |
|---|---|---|---|---|---|---|
| | 1 | | 5 | | 10 | |
| | FEL | $C_p$ | FEL | $C_p$ | FEL | $C_p$ |
| 1.0 | 82 | 14.2 | 91 | 15.1 | 96 | 17.4 |
| 3.0 | 75 | 12.6 | 98 | 16.9 | 95 | 17.9 |

What is claimed is:

1. A method of making an antimicrobial fabric characterized by the absence of release or diffusion of an antimicrobial agent comprising graft copolymerizing onto a base fabric or the fibers thereof, said base fabric or fibers thereof being selected from the group consisting of cotton, silk, wool, linen, rayon, cellulose acetate, synthetic polyester, acrylics, modacrylics, polyolefins, polyamides, poly(vinyl chloride), poly(vinyl alcohol), polyhydroxyacetic acid ester, polyurethanes, polytetrafluoroethylene, and copolymers thereof, polybenzimidazole, phenol-formaldehyde condensates, and blends thereof, a vinyl monomer having a first functional moiety and reacting the resulting graft copolymer with an antimicrobial agent having a second functional moiety where each functional moiety is independently selected from the group consisting of carboxyl, amino, epoxy, halogen, isocyanate, carbonyl, nitrile, and hydroxyl moieties, the reaction between first and second functional moieties resulting in irreversible covalent bond formation between the antimicrobial agent and the graft copolymer with production of an amide, ester, urea, urethane, ether, amine, or imine functional group, and recovering the resulting product.

2. The method of claim 1 where graft copolymerization is effected by irradiation or redox reagents.

3. The method of claim 1 where graft copolymerization is effected by electron beam, gamma, X-ray, or ultraviolet irradiation.

4. The method of claim 3 where the irradiation is electron beam.

5. The method of claim 2 where the redox reagent is selected from the group consisting of hydrogen peroxide, the ferrous ion-hydrogen peroxide couple, the hydrogen peroxide-thiourea couple, cerium(IV) salts, the diethylaluminum chloride-Co(III) couple, azoisobutyric acid dinitrile, Cr(VI) salts, and potassium persulfate.

6. The method of claim 1 where the antimicrobial is selected from the group consisting of the polymyxins, bacitracin, circulin, the octapeptins, lysozyme, lysostaphin, other cellulytic enzymes, vancomycin, ristocetin, the actinoidins, the avoparcins, tyrocidin A, gramicidin S, polyoxin D, tunicamycin, the polyene macrolide antibiotics, neomycin, streptomycin, and the penicillins.

7. A method of making an antimicrobial fabric comprising graft polymerizing onto a base fabric or fibers thereof selected from the group consisting of cotton, silk, wool, linen, rayon, cellulose acetate, synthetic polyesters, acrylics, modacrylics, polyolefins, polyamides, poly(vinyl chloride), poly(vinylidene chloride), poly(vinyl alcohol), poly(hydroxy acetic acid ester), polyurethanes, polytetrafluoroethylene, and copolymers thereof, polybenzimidazole, phenol-formaldehyde condensates, and blends thereof, an ethylenically unsaturated antimicrobial and recovering the resulting product.

8. The method of claim 7 where the antimicrobial naturally possesses at least one ethylenic site.

9. The method of claim 7 where the antimicrobial is covalently reacted with an ethylenically unsaturated reagent to afford an ethylenically unsaturated biologically active derivative prior to grafting.

10. The method of claim 7 where the graft copolymerization is effected by irradiation or redox reagents.

11. The method of claim 10 where graft copolymerization is effected by electron beam, gamma, X-ray, or ultraviolet irradiation.

12. The method of claim 11 where grafting is effected by electron beam irradiation.

13. The method of claim 10 where the redox reagent is selected from the group consisting of hydrogen peroxide, the ferrous ion-hydrogen peroxide couple, the hydrogen peroxide-thiourea couple, cerium(IV) salts, the diethyaluminum chloride-Co(III) couple, azoisobutyric acid dinitrile, Cr(IV) salts, and potassium persulfate.

14. An antimicrobial product characterized by the absence of release or diffusion of an antimicrobial agent covalently bonded thereto comprising a graft copolymer of a fabric or fibers thereof, said fabric or fibers being selected from the group consisting of cotton, silk, wool, linen, rayon, cellulose acetate, synthetic polyesters, acrylics, modacrylics, polyolefins, polyamides, poly(vinyl chloride), poly(vinylidene chloride), poly(vinyl alcohol), polyhydroxyacetic acid ester, polyurethanes, polytetrafluoroethylene, and copolymers thereof, polybenzimidazole, phenol-formaldehyde condensates, and blends thereof, with a vinyl monomer, said graft copolymer being irreversibly covalently bonded to an antimicrobial agent, the covalent bond being an amide, ester, urea, urethane, ether, amine, or imine bond resulting from reaction of a first functional moiety originating from the vinyl monomer and a second functional moiety originating from the antimicrobial, each of said functional moieties being independently selected from the group consisting of carboxyl, amino, epoxy, halogen, isocyanate, carbonyl, nitrile, and hydroxyl moieties.

15. The product of claim 14 where the fabric or fibers thereof is a cellulosic fabric.

16. The product of claim 15 where the fabric or fibers thereof is selected from the group consisting of cotton, linen, rayon, and cellulose acetate.

17. The product of claim 16 where the fabric or fibers thereof is cotton.

18. The product of claim 14 where the vinylic monomer is selected from the group consisting of acrylic acid and alkyl esters thereof, methacrylic acid and alkyl esters thereof, acrylonitrile, glycidyl acrylate, and glycidyl methacrylate.

19. The product of claim 14 where the antimicrobial is selected from the group consisting of the polymyxins, bacitracin, circulin, the octapeptins, lysozyme, lysostaphin, other cellulytic enzymes, vancomycin, ristocetin, the actinoidins, the avoparcins, tryocidin A, gramicidin S, polyoxin D, tunicamycin, the polyene macrolide antibiotics, streptomycin, neomycin, and the penicillins.

* * * * *